United States Patent [19]

Burke et al.

[11] Patent Number: 5,108,892
[45] Date of Patent: Apr. 28, 1992

[54] METHOD OF USING A TAQ DNA POLYMERASE WITHOUT 5'-3'-EXONUCLEASE ACTIVITY

[75] Inventors: Thomas J. Burke, Madison; David V. Thompson, Monona; Sandra L. Spurgeon, Madison, all of Wis.

[73] Assignee: Promega Corporation, Madison, Wis.

[21] Appl. No.: 389,745

[22] Filed: Aug. 3, 1989

[51] Int. Cl.$^5$ .................. C12Q 1/68; C12Q 19/34; G01N 33/566; G01N 33/48

[52] U.S. Cl. .......................... 435/6; 435/91; 435/280; 435/810; 436/501; 436/94; 935/77; 935/78

[58] Field of Search ............ 435/6, 91, 194, 280, 435/243; 436/501, 94; 935/77, 78

[56] References Cited

U.S. PATENT DOCUMENTS 4,889,818 12/1989 Gelfand et al. ............ 435/194

FOREIGN PATENT DOCUMENTS 0258017 2/1988 European Pat. Off. ............ 435/194

OTHER PUBLICATIONS

Bethesda Research Laboratories Life Technologies, Inc., promotional literature entitled "Dideoxy Sequencing Protocol for using BRL's High-Purity Test DNA Polymerase."
Bethesda Research Laboratories Lift Technologies, Inc., promotional literature entitled "High Purity Taq DNA Polymerase for Dideoxy Sequencing."
Bethesda Research Laboratories Life Technologies, Inc., "Highly Purified DNA Polymerase from *Thermus aquaticus*," D'Alession, J. M., et al., *Focus* 11:2, pp. 30–31.
Chien et al., 1976, *Journal of Bacteriology*, vol. 127, No. 3, pp. 1550–1557.
Freifelder, David, 1976, *Physical Biochemistry*, W. H. Freeman and Company, pp. 217–220.
Heiner, C. et al., 1988, *Applied Biosystems, Inc. DNA Sequencer Model 370 User Bulletin-Taqu Polymerase: Increased Enzyme Versatility in DNA Sequencing.*
Higuchi, R. et al., 1988, *Nucleic Acids Research*, vol. 16, No. 15, pp. 7351–7367.
Hong, G. F., 1982, *Bioscience Reports*, vol. 2, pp. 907–912.
Innis et al., 1988, *Proc. Natl. Acad. Sci. USA*, vol. 85, pp. 9436–9440.
Kaledin et al., 1980, translated from *Biokhimiya*, vol. 45, No. 4, pp. 644–651.
Labeit, S. 1987, *Methods in Enzymology*, vol. 155, pp. 166–177.
Lawyer, F. C. et al., 1988, *J. Biol. Chem.*, vol. 264, No. 11, pp. 6427–6437.
Lo, Y-M. D. et al., 1988, *Nucleic Acids Research*, vol. 16, No. 17, p. 8719.
McGraw, R. A., 1984, *Anal. Biochem.*, vol. 143, pp. 298–303.
*Promega Notes* No. 16 (Nov. 1988) describes the Taq-Track ™ DNA Sequencing System.

Primary Examiner—Robert A. Wax
Assistant Examiner—Stephanie W. Zitomer

[57] ABSTRACT

The present invention is directed to a modified Taq DNA polymerase and methods for its use.

46 Claims, 3 Drawing Sheets

*Molecular Weight Marker

FIGURE 1

SEQUENCING PRODUCTS

PRIMER      5'caggaaacagctatgac3'
TEMPLATE   3'gtcctttgtcgatactggtagcgactgctggtttcgggcactggtcatcgtcctg5'

END LABEL PRODUCTS

| | |
|---|---|
| Caggaaacagctatgaccatcgctgacgaccaaagcccgtgacc | 44 bases, c terminus |
| Caggaaacagctatgaccatcgctgacgaccaaagcccgtgaccag | 46 bases, g terminus |
| Caggaaacagctatgaccatcgctgacgaccaaagcccgtgaccagta | 48 bases, a terminus |

EXTENSION/LABEL PRODUCTS

| | |
|---|---|
| caggaaacagctatgaccAtcgctgAcgaccaAagcccgtgAcc | 44 bases, c terminus |
| caggaaacagctatgaccAtcgctgAcgaccaAagcccgtgAccag | 46 bases, g terminus |
| caggaaacagctatgaccAtcgctgAcgaccaAagcccgtgAccagta | 48 bases, a terminus |

END LABEL PRODUCTS WITH 5' -> 3' EXONUCLEASE

| | |
|---|---|
| Caggaaacagctatgaccatcgctgacgaccaaagcccgtgacc | 44 bases, c terminus |
| ggaaacagctatgaccatcgctgacgaccaaagcccgtgaccag | 44 bases, g terminus (NR) |
| ggaaacagctatgaccatcgctgacgaccaaagcccgtgaccagta | 46 bases, a terminus (NR) |

EXTENSION/LABEL PRODUCTS WITH 5'->3' EXONUCLEASE

| | |
|---|---|
| caggaaacagctatgaccAtcgctgAcgaccaAagcccgtgAcc | 44 bases, c terminus |
| ggaaacagctatgaccAtcgctgAcgaccaAagcccgtgAccag | 44 bases, g terminus |
| ggaaacagctatgaccAtcgctgAcgaccaAagcccgtgAccagta | 46 bases, a terminus |

*(NR) = non-radioactive

METHOD OF USING A TAQ DNA POLYMERASE WITHOUT 5'-3'-EXONUCLEASE ACTIVITY

FIELD OF THE INVENTION

The present invention is generally directed to DNA polymerases. The present invention is more specifically directed to a modified thermostable DNA polymerase, which is purified from *Thermus aquaticus,* having an apparent molecular weight of about 80,000 daltons. The present invention is further directed to the use of the modified thermostable DNA polymerase in DNA sequencing.

DESCRIPTION OF THE PRIOR ART

Deoxyribonucleic acid (DNA) is a complex biological molecule, found in cells, that carries and transmits the genetic information in all living things. DNA carries within its structure the hereditary information that determines the structures of proteins, the basic building blocks of all cells.

The basic structure of DNA is formed from four nucleotide bases: adenine (A), thymine (T), cytosine (C) and guanine (G). The nucleotide bases are linked to form strand of DNA. It is the order or sequence of the bases a strand of DNA which determines which gene is present and ultimately which protein will be synthesized.

The accurate determination of nucleotide base sequences comprising a genetic element is a prerequisite to further understanding the structure and function of the proteins produced by the encoded information. One such method, DNA sequencing, involves the determination of the order in which the nucleotide bases are arranged within a length of DNA. A number of different DNA sequencing techniques are available, including either enzymatic analysis or chemical hydrolysis. The emphasis in this application is on DNA sequencing by enzymatic means. As a result, chemical DNA sequencing will not be addressed here.

One enzymatic method, known as the dideoxy or extension/termination method, uses enzyme and chain-terminating dideoxy nucleotide analogs in the enzymatic synthesis of a DNA strand. This method is preferred because it is considered faster and less labor intensive than sequencing by chemical means. The dideoxy method is based on the ability of a DNA polymerase to extend a primer, hybridized to the template that is to be sequenced, until a chain-terminating nucleotide is incorporated.

The procedure initiates by hybridizing a primer, preferably an oligonucleotide primer, to the DNA template to be sequenced. It is critical to have a well-defined starting nucleotide at the 5' end of the primer in the synthesis reaction. The DNA polymerase extends the oligonucleotide primer until a strand-terminating dideoxy nucleotide is incorporated therein. The resulting fragments, each with a common origin but ending in a different nucleotide, are separated according to size by high-resolution denaturing gel electrophoresis.

The basis of dideoxy sequencing is the ability of nucleotide analogs to terminate elongating DNA strands. Each sequence determination is generally carried out as a set of four separate reactions, each of which contains all four normal deoxynucleotide triphosphates (dNTPs) supplemented with a limiting amount of a different dideoxyribonucleotide triphosphate (ddNTP). Each population of fragments begins at the same precise nucleotide position, but has a variable terminus at one of the four nucleotides: A, T, C and G. Because the ddNTP lacks the necessary 3'-OH group required for chain elongation, the growing oligonucleotide is terminated selectively at one of the following nucleotide bases: G, A, T or C, depending on the respective dideoxy analog in the reaction. The relative concentrations of each of the dNTPs and ddNTPs can be adjusted to give a nested set of DNA strands ranging in length from a few hundred to a few thousand bases. See Watson, J.D., et al., 1987, *Molecular Biology of the Gene,* The Benjamin/Cummings Publishing Company, Inc., California, pp. 274-276 for further details on DNA sequencing in general.

The incorporation of a radiolabel somewhere in the oligonucleotide chain permits the visualization of the sequencing products by autoradiography. Three basic radiolabeling protocols have been utilized to detect the reaction products. The original method, developed by Sanger, F., et al. (1977, *Proc. Natl. Acad. Sci. USA,* Vol. 74, pp. 5463-5467) combines the labeling and the primer extension/chain termination portions of the reaction into one step by lowering the concentration of one of the four dNTPs and employing the same radioactively labeled dNTP. The basic procedure involves (a) hybridizing an oligonucleotide primer to a suitable single—or denatured double-stranded—DNA template; (b) extending the primer with DNA polymerase, an enzyme which makes DNA copies from a DNA template, in four reaction mixtures containing one alpha-labeled dNTP, a mixture of unlabeled dNTP's and one chain-terminating ddNTP; (c) resolving the four sets of reaction products on a high-resolution polyacrylamide/urea gel electrophoresis; and (d) producing an autoradiographic image of the gel, which can be examined to infer the DNA sequence.

The second method, developed by Tabor, S. and C.C. Richardson (1987, *Proc. Natl. Acad. Sci. USA,* Vol. 84, pp. 4767-4771), separates the sequencing reaction into a labeling step and an extension/termination step. In this method, the primer is first extended a short distance using limiting concentrations of the dNTP's, one of which is radiolabeled. In a second step, the extended primers are further extended in the presence of both dd- and dNTPs. The remainder of the procedure is described by Sanger, et al. (supra.).

In a third method, a radioactive or nonradioactive label is directly attached to the end of the primer. See Hong, G.F. (1982) *Bioscience Reports,* Vol. 2, p. 907, and McGraw, R.A. (1984) *Anal. Biochem.,* Vol. 143, p. 298. For isotopic labeling, the oligonucleotide is 5' end-labeled using T4 polynucleotide kinase and [gamma-$^{32}$P] ATP or [gamma-$^{35}$S] ATP.

Over the years, several modifications have been made to the process of dideoxy DNA sequencing. For example, there are now several commonly used sequencing enzymes, among them the Klenow fragment of DNA polymerase I, avian reverse transcriptase and bacteriophage T7 DNA polymerase. Further, the use of $^{35}$S or non-radioactively labeled nucleotides such as biotin or fluorescently labeled nucleotides instead of $^{32}$P for DNA detection is becoming more common. Reference is made to Heiner, et al. (infra. at page 22) for the use of non-radioactively labeled nucleotides. Additionally, the use of 7-deaza guanosine has become fairly common to reduce banding compression during polyacrylamide gel electrophoresis (PAGE).

One requirement of a DNA sequencing technique, such as the dideoxy method, is that the exact number of nucleotides from the known starting site to the variable terminus must be known for reliable DNA sequences to be detected. If the starting nucleotide is slightly variant among fragments, the two fragments may terminate with different nucleotides, but have the same length. Likewise, two fragments may terminate with the same nucleotide, but have different lengths. These make DNA sequence interpretation difficult, if not impossible.

It is also known that ordinary sequencing reactions are performed at temperatures between 20°-37° C. However, it has been demonstrated that sequencing at elevated temperatures allows polymerases to sequence better. Such DNA polymerases which can sequence at a higher temperature include Klenow (50° C.) and T7 DNA polymerase (45° C).

A thermostable DNA polymerase from *Thermus aquaticus*, known as Taq DNA polymerase, has also be utilized for DNA sequencing. This enzyme has a temperature optimum of 70°-80° C., and sequencing DNA at these temperatures overcomes difficulties commonly seen in reactions performed at lower temperatures.

DNA polymerase from *Thermus aquaticus* was first purified and characterized by Chien, et al. (1976), *Journal of Bacteriology*, Vol. 127, No. 3, pp. 1550-1557. The native molecular weight of a single native enzyme was reported to be approximately 63,000-68,000 daltons as determined by sucrose gradient centrifugation and gel filtration on Sephadex G-100.

The purification and characterization of Taq DNA polymerase was also described by Kaledin, et al. (1980), translated from *Biokhimiya*, Vol. 45, pp. 644-651. Molecular weights of 60,000 and 62,000 daltons were reported as determined by sucrose gradient centrifugation and SDS-PAGE, respectively. Reference is also made to European patent application publication No. 258,017, in which the molecular weight of Taq DNA polymerase is reported to be approximately 86,000-90,000 daltons.

Reference is also made to Innis, et al. (1988), *Proc. Natl. Acad. Sci. USA*, Vol. 85, pp. 9436-9440, which reports that a single subunit Taq DNA polymerase with an apparent molecular weight of about 96,000 daltons was functional in DNA sequencing. A cloned version of Taq polymerase with an apparent molecular weight of approximately 94,000 daltons was also used to sequence DNA.

The isolation, characterization and expression in *Escherichia coli* of the Taq DNA polymerase gene was reported by Lawyer, F.C., et al. (1989), *J. Biol. Chem.*, Vol. 264, No. 11, pp. 6427-6437. Active full-length and truncated forms of the enzyme were produced with molecular weights of approximately 94,000 and 65,000 daltons.

The Bethesda Research Laboratories Life Technologies, Inc. has also distributed promotional literature claiming that an 80,000 dalton polymerase had been purified, and it was suggested that this protein may be a cleavage product of an 85,000 dalton protein. No claim was made that the 80,000 dalton protein could sequence DNA or if the enzymatic activity of the two polymerases differed in any way.

While a thermostable DNA polymerase isolated from *Thermus aquaticus* is known to be useful for DNA sequencing, the polymerases in the prior art suffer the disadvantage of having 5'-3' exonuclease activity as observed in DNA sequencing reactions. This means that the DNA polymerase enzyme cleaves nucleic acids at the 5' ends of the DNA primers. Because it is vitally important to know the exact number of nucleotides from the known starting site to the variable terminus for reliable DNA sequencing, if the starting nucleotide is variant among fragments, the two fragments may terminate with different nucleotides even though they have the same length. This makes DNA sequence interpretation difficult, if not impossible. In other words, when used in DNA sequencing, an unmodified Taq polymerase exhibits a significant 5'-3' exonuclease activity. The 5'-3' exonuclease activity in DNA sequencing and resulting degradation of a primer from the 5' end means that the starting nucleotide in a reaction could be variable making proper interpretation of DNA sequencing data extremely difficult.

SUMMARY OF THE INVENTION

The present invention is directed to a modified form of Taq DNA polymerase, its manufacture and its use in DNA sequencing. The enzyme can be purified so that the apparent molecular weight by SDS-PAGE is approximately 85,000 daltons, herein referred to as the unmodified polymerase. A procedure has now been developed for the production of a polymerase with an apparent molecular weight of about 80,000 daltons, herein referred to as the modified Taq DNA polymerase. The 80,000 dalton molecular weight polymerase exhibits substantially no 5'-3' exonuclease activity and is therefore the preferred enzyme for DNA sequencing.

The use of modified Taq DNA polymerase results in sequencing data exhibiting a consistent sharp, clean band intensity, a low background, and minimal detectable exonuclease activity to interfere with DNA sequence determination, making the DNA sequence easy to read. The modified Taq DNA polymerase can be used in both manual and automated sequencing because it is highly processive. The enzyme is stable at high temperatures for periods well beyond those required for standard sequencing protocols. The higher reaction temperature of the sequencing system, i.e., at temperatures between 70°-95° C., decreases the secondary structure of DNA templates and permits polymerization through highly structured regions. The higher temperature also increases the stringency of primer hybridization which reduce base-pair mismatch and unwanted background.

Sequencing with modified Taq DNA polymerase produces readable DNA sequence data from 1-500 bases, and preferably up to 1000 bases, with a single-stranded (ss) DNA template. The modified Taq DNA polymerase sequencing system can also be used with double-stranded (ds) templates such as amplified DNA, large ds DNA templates such as lambda, GC-rich templates and long poly (A) tails.

The present invention is directed to a method for determining the nucleotide base sequence of a DNA molecule comprising hybridizing a primer to a DNA template molecule to be sequenced. The primer is then extended with a modified Taq DNA polymerase having an apparent molecular about 80,000 daltons and substantially no 5'-3' exonuclease activity. A strand terminating nucleotide is then incorporated onto the extending primer under conditions to yield a distinct population of nucleotide fragments beginning at the same nucleotide position for all populations and having a variable terminus at one of the following four nucleotide bases: A, C, G, and T. The synthesized nucleotide fragments are then separated according to size, whereby at least a part of the nucleotide base sequence of the DNA molecule can be determined.

Another method for determining the nucleotide base sequence of a DNA molecule involves hybridizing an olignonucleotide primer to a template of the DNA molecule to be sequenced; extending the primer with a modified Taq DNA polymerase having an apparent molecular weight of about 80,000 daltons; incorporating a strand terminating nucleotide onto the extended primer, wherein the determination of the DNA sequence is accomplished by a set of four different sequencing reactions, wherein each sequencing reaction contains a different strand terminating nucleotide which terminates nucleotide synthesis at a specific nucleotide base wherein each reaction yields a distinct population of nucleotide fragments beginning on the same nucleotide position for all populations, but having a variable terminus at one of the following four nucleotide bases: A, C, G, and T; and separating the synthesized fragments according to their size, whereby at least a part of the nucleotide base sequence of the DNA molecule can be determined.

The present invention is also directed to an enzymatic DNA synthesis reaction wherein a primer is hybridized to a template DNA molecule to be replicated. The improvement includes extending the primer with a modified Taq DNA polymerase having an apparent molecular weight of about 80,000 daltons and substantially no 5'-3' exonuclease activity.

The present invention is further directed to a method of amplifying a DNA sequence comprising annealing a first and second primer to opposite strands of a double-stranded DNA sequence, and thermocycling the annealed mixture with a modified Taq DNA polymerase having an apparent molecular weight of about 80,000 daltons and substantially no 5'-3' exonuclease activity, wherein the first and second primers anneal to opposite strands of the DNA template sequence. The present invention is also directed to an amplified DNA sequence comprising multiple copies of the sequence produced by the amplification process as described in this paragraph.

The present invention is also directed to a process for the manufacture of a modified Taq DNA polymerase having an apparent molecular weight of about 80,000 daltons, comprising culturing *Thermus aquaticus* cells, disrupting the *Thermus aquaticus* cells, purifying the DNA polymerase from the *Thermus aquaticus* cells, and assaying a DNA polymerase of *Thermus aquaticus* with a molecular weight of about 80,000 daltons.

The present invention is also directed to a thermocycling sequencing method comprising denaturing the DNA sequence under suitable denaturing conditions to form single-stranded DNA sequence segments, annealing the DNA sequence under conditions sufficient to hybridize a primer to a template of a DNA sequence segment, and replicating the DNA sequence segment by extending the primer with a modified Taq DNA polymerase having an apparent molecular weight of about 80,000 daltons.

The present invention is also directed to a method for determining the order in which nucleotide bases are arranged within a nucleic acid strand, comprising incubating the nucleic acid strand in an appropriate buffer with a nucleotide triphosphate selected from the group consisting of dATP, dCTP, dGTP, dTTP, and a primer for each sequence, and incubating the nucleic acid strand at the same time with a modified Taq DNA polymerase having an apparent molecular weight of about 80,000 daltons and substantially no 5'-3' exonuclease activity for an effective time and at an effective temperature to catalyze the nucleotide triphosphate to form primer extension products complementary to each nucleic acid strand.

The present invention is also directed to a method for labeling DNA molecules comprising annealing a primer to a DNA template molecule, and incubating a labeling nucleotide in the aneealed mixture with a modified Taq DNA polymerase having an apparent molecular weight of about 80,000 daltons and substantially no 5'-3' exonuclease activity under effective conditions to incorporate the labeled nucleotide into the DNA molecule.

The present invention is further directed to a method for site-directed in vitro mutagenesis within a DNA sequence. The method includes annealing a primer containing a desired mutation sequence to a DNA template molecule and extending the primer with a modified Taq DNA polymerase having a molecular weight of about 80,000 daltons and substantially no 5'-3' exonuclease activity, such that the primer synthesizes a new DNA sequence containing the mutation.

Additionally, the present invention is directed to a method for random in vitro mutagenesis within a DNA sequence. The method includes annealing a primer to the DNA sequence in the presence of modified Taq DNA polymerase having a molecular weight of about 80,000 daltons and substantially no 5'-3' exonuclease activity, under conditions in which the DNA sequence is randomly mutated as the new DNA strand is synthesized.

The present invention is further directed to a kit for DNA sequencing comprising a modified Taq DNA polymerase having an apparent molecular weight of about 80,000 daltons and substantially no 5'-3' exonuclease activity, and appropriate reagents necessary for sequencing. The reagents are selected from deoxyribonucleotides, chain-terminating agents, DNA sequencing primers, reaction buffers and mixtures thereof.

Other applications include the use of modified Taq DNA polymerases in mutagenesis, radioactively labeling DNA, non-radioactively labeling DNA, second strand cDNA synthesis and any additional primed DNA synthesis procedures.

Further objects, features and advantages of the invention will be apparent from the following detailed description when taken in conjunction with the accompanying drawings.

DETAILED DESCRIPTION OF THE INVENTION

Definitions

For purposes of the present application, the terms listed herein will be accorded the following definitions:

The "apparent molecular weight" of a protein is the molecular weight as determined by sodium dodecyl sulphate polyacrylamide gel electrophoresis (SDS-PAGE). SDS-PAGE is a specialized form of electrophoresis used, e.g., for determining the molecular weight of a protein, or for separating mixtures of proteins. See Freifelder, David (1976), *Physical Biochemistry*, W.H. Freeman and Company, pp. 217-220, for a more detailed explanation of SDS-PAGE. When a protein of unknown molecular weight is electrophoresed with proteins of known molecular weight, the apparent molecular weight of the unknown protein can be calculated to an accuracy ranging from between about 5% and 10%. Several factors subtly influence the apparent molecular weight determination of protein, including the percentage of acrylamide in the gel, the relative quantities of protein in the electrophoresis samples, the distance of migration, and the rate of electrophoresis. The apparent molecular weights of the modified and unmodified Taq DNA polymerases described herein vary slightly from trial to trial. The unmodified polymerase (described as the 85,000 dalton protein) and the modified polymerase (described as the 80,000 dalton protein) may have slightly higher or lower apparent molecular weights for any given determination. The ascribed numbers reflect typical molecular weight measurements. Only two polymerase proteins have been identified in this invention within the general molecular weight range described here. Others may describe the 85,000 dalton molecular weight polymerase with a higher or lower apparent molecular weight, but the modified polymerase is approximately 5,000-7,000 daltons smaller and exists as a stable, presumably single, entity.

The term "band intensity" is a term used to describe single strength autoradiography. Autoradiography is used to determine the presence of radioactively labeled molecules by their effect in creating an image on photographic film. In a polyacrylamide gel, any given set of equivalently sized DNA fragments will comigrate in a given band-like position. The intensity of the band-like image captured on film, i.e., band intensity, is proportional to the amount of radioactivity in the DNA within the band.

The term "DNA polymerase" is used to describe an enzyme which polymerizes deoxyribonucleotides by condensing dNTPs with the elimination of pyrophosphate. The enzyme must be primed.

The term "exonuclease activity" is used to describe activity ascribed to an enzyme which catalyzes the removal of nucleotides from one end of a strand of nucleic acid. Various assays have been described to measure 5'-3' exonuclease activity, but DNA sequencing is one of the most sensitive. The removal of 1-2 bases from the end of a sequencing primer can be detected in a sequencing reaction.

The term "hybridization" is used herein to describe the complementary formation of a double-stranded nucleic acid by base-pairing between single-stranded nucleic acids.

The term "nucleotide base sequence" is used to describe a linear array of nucleotides in a DNA molecule commonly made up of four dNTPs: dATP, dCTP, dGTP and dTTP. Modified bases, other than the usual four found in DNA, may also be incorporated.

The term "primer" is used to describe a sequence of DNA (or possibly RNA) that is paired with one strand of DNA and provides a free 3'-OH at which a DNA polymerase starts synthesis of a deoxyribonucleotide chain. Preferably, the primer is composed of an oligonucleotide.

The term "strand terminating nucleotide" is used to describe a nucleotide which stops elongation of a DNA strand by a DNA polymerase.

The term "thermostable enzyme" is used to describe an enzyme which is generally not irreversibly denatured by relatively high temperatures. High temperatures are temperatures which are significantly higher than the optimum growth temperature of the organism from which the enzyme is isolated.

Modified Taq DNA Polymerase

The present invention is directed to the formation and use of a modified thermostable DNA polymerase from *Thermus aquaticus*, hereinafter known as modified Taq DNA polymerase. There are a number of strains of *Thermus aquaticus* available, however, the preferred strain for use herein is YT-1.

The enzyme can be purified so that the apparent molecular weight by SDS-PAGE is approximately 85,000 daltons for the unmodified form of the polymerase. A procedure has now been developed for the production of a polymerase with an apparent molecular weight of about 80,000 daltons, hereinafter referred to as modified Taq DNA polymerase.

When used in DNA sequencing, the unmodified polymerase exhibits a significant 5'-3' exonuclease activity. On the other hand, the 80,000 dalton molecular weight modified polymerase shows substantially no 5'-3' exonuclease activity and is therefore the preferred enzyme for DNA sequencing.

Figure 3:
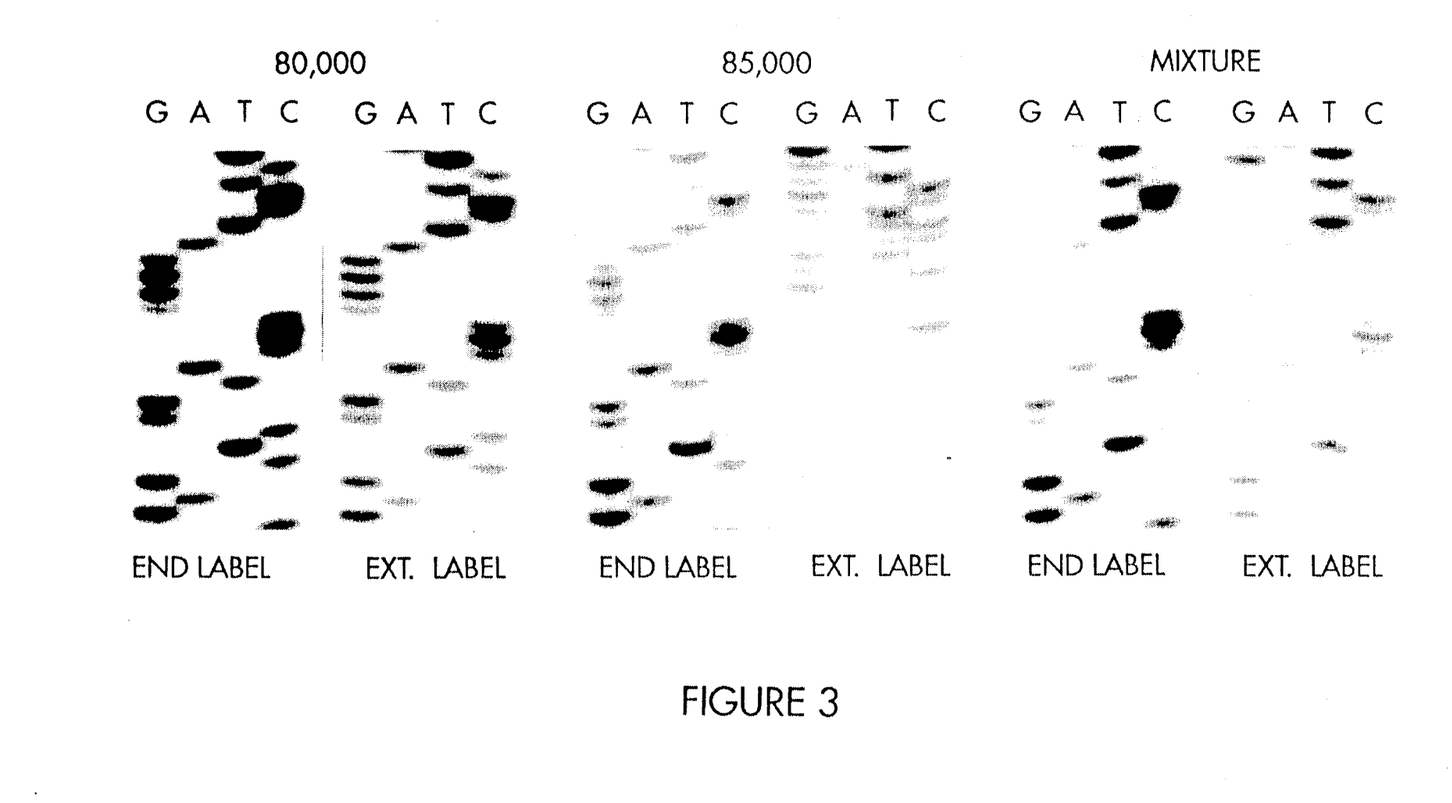
FIG. 3 is an autoradiograph illustrating the DNA sequence analysis using Taq DNA polymerase. DNA sequence analysis was performed using the modified Taq DNA polymerase (80,000 dalton molecular weight), the unmodified DNA polymerase (85,000 dalton molecular weight) and both polymerases. Each enzyme was used in both the end labeled (END LABEL) procedure and the extension/label (EXT LABEL) procedure to sequence a denatured double-stranded plasmid template. The four lanes are denoted G, A, T, C to read the sequence.

The significance of 5'-3' exonuclease activity in DNA sequencing is that the degradation of a primer from the 5' end means that the starting nucleotide in a reaction could be variable. As described above, this makes interpretation of DNA sequencing data difficult if not impossible. Reference is also made to FIG. 3 which will be described hereinafter.

To produce reliable sequence data, it is critical that the 5' end of a synthesized strand be invariable for all four reactions. The exonuclease removes nucleotides from the 5' end of the synthesized DNA strand making a variable starting nucleotide. It therefore becomes difficult to correlate the distinct size of a fragment with the presence of a particular nucleotide at the 3' end and therefore, the determination of the DNA sequence is made more difficult. With the modified Taq DNA polymerase, however, there is little or no detectable 5'-3' exonuclease activity. Use of the modified Taq polymerase allows the distinct and unambiguous electrophoretic separation of DNA fragments and thereby generates reliable sequence data.

As a sequencing enzyme, modified Taq DNA polymerase exhibits consistent band intensity, low background and minimal detectable exonuclease activity to interfere with the DNA sequence determination. The enzyme is stable at high temperatures for periods well beyond those required in standard sequencing protocols. The higher reaction temperature of the sequencing system, at temperatures to about 96° C., preferably between about 70° and 95° C., and most preferably between about 70° and 80° C., decreases the secondary structure of DNA templates and thus permits polymerization through highly structured regions. The higher temperature also increases the stringency of primer hybridization which decreases non-specific binding and unwanted background. Additionally, the modified Taq DNA polymerase is catalytically active at temperatures up to about 80° C. and preferably between about 70° C. and about 80° C. The modified Taq DNA polymerase does not discriminate against nucleotide analog incorporation; that is, the possibility of incorporating an analog is about the same as that of a normal nucleotide. The modified Taq DNA polymerase of the present invention is also able to use small primers, i.e., primers having fifteen bases or less.

Manufacture of Modified Taq DNA Polymerase Having a Molecular Weight of 80,000 Daltons While not being constrained to any one particular theory on the formation of the modified Taq DNA polymerase, it is believed that this lower molecular weight polymerase is a modified product of the unmodified higher molecular weight Taq DNA polymerase. It is reasoned that the modification inactivates a domain involved in polymerase-associated and possibly polymerization-dependent 5'-3' exonuclease activity. The exact nature of the modification is unknown. However, a proteolytic cleavage event is consistent with all of the observed data. This does not exclude any other protein modifying reactions which alter the molecular weight.

The protocol for producing modified Taq DNA polymerase, which has an apparent molecular weight of 80,000 daltons as determined by SDS-PAGE, is accomplished by several steps. First, *Thermus aquaticus* YT1 cells are grown in a medium containing 3 grams/liter (g/l) yeast extract, 3 g/l tryptone, 5 g/l sodium succinate, 0.7 g/l sodium nitrate, 0.1 g/l potassium nitrate, 0.1 g/l calcium nitrate, 0.1 g/l magnesium sulfate, and trace elements essentially as described by Kaledin, et al., 1980 (supra.). The pH is adjusted to 8.0±0.2 with KOH and the dissolved oxygen is maintained at greater than 10%. The cells are fermented at 70° C. and harvested in a Sharples centrifuge with a throughput of approximately 2.8 liters/minute when the dissolved oxygen levels begin to rise. Normally, fermentation involves about 18 hours of growth. Following fermentation, the *Thermus aquaticus* cells may be stored frozen at a temperature of −70° C. until needed.

The extract of *Thermus aquaticus* cells is prepared by suspending 1 kilogram (kg) of frozen *Thermus aquaticus* cells in 800 milliliters (ml) 0.25M NaCl in TEBG buffer (50 mM Tris-HCl, pH 7.3 at 25° C., 1 mM EDTA, 0.1% 2-mercaptoethanol, and 10% glycerol) by blending. The cells are broken by passing them four to six times in a Mantin-Gaulin press at maximum pressure, keeping the temperature below 37° C. The total volume is then adjusted to 2200 ml. Following this, solid polyethylene glycol (PEG) 6000-8000 (Sigma) is added to 7.5% (w/v) and stirred 1.5 hours at 4° C. The extract is then centrifuged overnight at 17,000×g. The supernatant is then decanted and allowed to stand at 4° C. for 36 hours. The extract is then dialyzed in TEBG until the salt concentration is less than 30 mM.

The dialyzed sample is then applied to a 1.2 liter DEAE Sepharose (FF) (Pharmacia) column (5 cm diameter) equilibrated in TEBG. The column is then washed with 2-4 liters TEBG. The column is eluted with a linear gradient with 2.5 liters of 0-0.5M NaCl in TEBG. Twenty-five ml fractions are collected and assayed for DNA polymerase activity. The fractions which contain greater than 5% of the total activity are then pooled. No dialysis is necessary for the next column.

The pooled fractions are applied to a 300 ml Affigel Blue column (BioRad) (5 cm diameter) and equilibrated in TEBG. The loaded column is washed with 3-4 liters TEBG. The column is then eluted with a linear gradient of 2 liters of 0-1.5M NaCl in TEBG. Twenty-five ml fractions are then collected and assayed for polymerase activity. The fractions with more than 5% of the polymerase activity are then pooled and dialyzed in TEBG so that the NaCl concentration is less than 75 mM.

The dialyzed pool is then applied to a 200 ml DNA-Sepharose column (2.5 cm diameter) and equilibrated in TEBG. The flow rate should be less than 50 ml/hr. The column is washed with 1.5-2.0 liters TEBG at a flow rate of less than 100-200 ml/hr. The column is eluted with a linear gradient of 800 ml of 0-0.5M NaCl in TEBG at less than 50 ml/hr. Ten milliliter fractions are collected and the polymerase activity is measured. The DNA polymerase activity elutes at approximately 0.21M NaCl. A sample of each fraction containing polymerase activity is then analyzed for molecular weight using, for example, SDS-PAGE (10% resolving gel) and Coomassie blue staining. The fractions in which the 80,000 molecular weight polymerase is more than 80% of the Taq polymerase present are then pooled. Triton X-100 (Pierce) is then added to 0.1% and dialyzed in TEBG containing the same amount of detergent.

The pooled fractions are then applied to a 20 ml Mono Q column (Pharmacia) and equilibrated in TEBG/0.1% Triton X-100. The loaded column is washed with 120 ml TEBG and eluted with 300 ml of 0-0.1M NaCl in TEBG. Polymerase activity assays are performed and the fractions are checked for contaminating nucleases by doing digestions of lambda DNA from a sample of each column fraction. The polymerase activity is then pooled while avoiding the nuclease activity. A time course unit assay is then performed to determine the total amount of activity present. The DNA polymerase is dialyzed into the appropriate amount of storage buffer (50% glycerol, 50 mM Tris-HCl at pH 8.0 and temperature 25° C., 100 mM NaCl, 0.1 mM EDTA, 1 mM dithiothreitol, 200 ug/ml gelatin and 0.1% Triton X-100) so that activity is 5000-7000 units/ml.

The unit activity of Taq DNA polymerase, as mentioned above, is measured using activated calf thymus DNA as the template Activated DNA is prepared by partial digestion with DNase I until 5% of the nucleotides are acid soluble. One unit of polymerase is the amount of enzyme required to incorporate 10 nmoles of dNTPs into acid insoluble material in 30 minutes at 74° C. Activity specifications for the following sequencing applications require that the enzyme concentration be not less than 5000 units ml and not greater than 7000 units ml. Individual activity measurement should establish the activity within + or −20%.

The standard time course assay is set up to allow unit activities to be determined at four times (6, 9, 12 and 15 minutes) during a 15 minute reaction. For preparation of the reaction mixture for a Taq DNA polymerase unit assay, 48 ul of activated calf thymus DNA (2.1 ug/ul) are mixed with 40 ul 10X assay buffer containing 500 mM Tris-HCl at pH 9 and temperature 25° C., 500 mM NaCl, and 100 mM MgCl$_2$, along with 40 microliters (ul) 10X dNTPs (2 mM dATP, 2 mM dCTP, 2 mM dGTP and 0.5 mM dTTP), 8 ul $^3$H TTP (8 uCi; 35-45 Ci/mmole) (Amersham) and 256 ul water. 245 ul and 5 ul of Taq DNA polymerase diluted 1:100 in 1× assay buffer is gently mixed, but not vortexed. The reaction proceeds at 74° C.

Fifty microliter samples are then removed at 6, 9, 12 and 15 minute intervals and immediately added to 0.5 ml cold 10% TCA in a 0.5 ml microfuge tube on ice. After 10–30 minutes on ice, the entire TCA precipitation is filtered through a Whatman GFA filter. The microfuge tube is rinsed out with 3 volumes of cold 5% TCA and the filters washed twice with 10 mls of cold 5% TCA and 10 mls of acetone. The filters are dried and the bound radioactivity is counted and calculated for unit concentration.

Manufacture of Unmodified Taq DNA Polymerase Having a Molecular Weight of 85,000 Daltons The following steps are necessary for producing unmodified Taq DNA polymerase, which has an apparent molecular weight of 85,000 daltons as determined by SDS-PAGE. To produce the higher molecular weight polymerase, it is important to complete all steps through chromatography of the first column as rapidly as possible. Significant protein modification can occur between the time the cells are broken through the first chromatographic step.

The fermentation of *Thermus aquaticus* is similar to that described above with respect to the modified Taq DNA polymerase. After the *Thermus aquaticus* has been cultured, 1 kilogram (kg) of the frozen *Thermus aquaticus* cells is suspended in 800 ml TEBG buffer. The cells are then broken in a Mantin-Gaulin press with 3 to 4 passes at maximum pressure keeping the temperature below 15° C. The volume of the cells is brought to 2200 ml with TEBG. Polyethyleneimine (Sigma) is then added to 1% (v/v). The mixture is stirred for 30 minutes at 4° C. and centrifuged for 45 minutes at 18,000 rpm. The supernatant is then decanted and ammonium sulfate is added to 80% saturation. The resulting mixture is stirred at 4° C for 1 hour and centrifuged at 47,000×g. for 1 hour. The pellet is suspended in 1 liter TEBG and dialyzed in TEBG. Alternatively, PEG 6000–8000 may be added to 7.5% (w/v) instead of polyethyleneimine. If this is done, the ammonium sulfate precipitation should be omitted.

The chromatography assay is performed on a DEAE Sepharose column as follows. The dialyzed sample is applied to a 1.2 liter DEAE Sepharose column (5 cm diameter) equilibrated in TEBG. The column is washed with 2 liters TEBG. The column is eluted with a linear gradient of 2.5 liters 0–0.5M NaCl in TEBG. Twenty-five ml fractions are collected and assayed for DNA polymerase activity as described previously with respect to the unmodified Taq DNA polymerase. Based on incorporated cpm of $^3$H-TTP in the assay, the fractions which contain greater than 5% of the total activity are pooled. No dialysis is necessary for the next column.

The Affigel Blue chromotography assay is performed according to the directions specified with respect to the unmodified Taq DNA polymerase above. To prevent modification of the Taq DNA polymerase, the protein should be chromatographed as fast as possible and not allowed to warm to above 4° C. After the Affigel Blue column elution, very little modification is seen. All column fractions collected from the DNA Sepharose and Mono Q columns which contain DNA polymerase activity are analyzed by SDS-PAGE. Only samples in which the 85,000 dalton molecular weight polymerase is greater than 95% of the polymerase protein should be pooled. Both the unit definition and the activity assays are performed in the same manner as described above with respect to the modified Taq DNA polymerase.

Analysis of the Modified and Unmodified Taq DNA Polymerase

Figure 1:
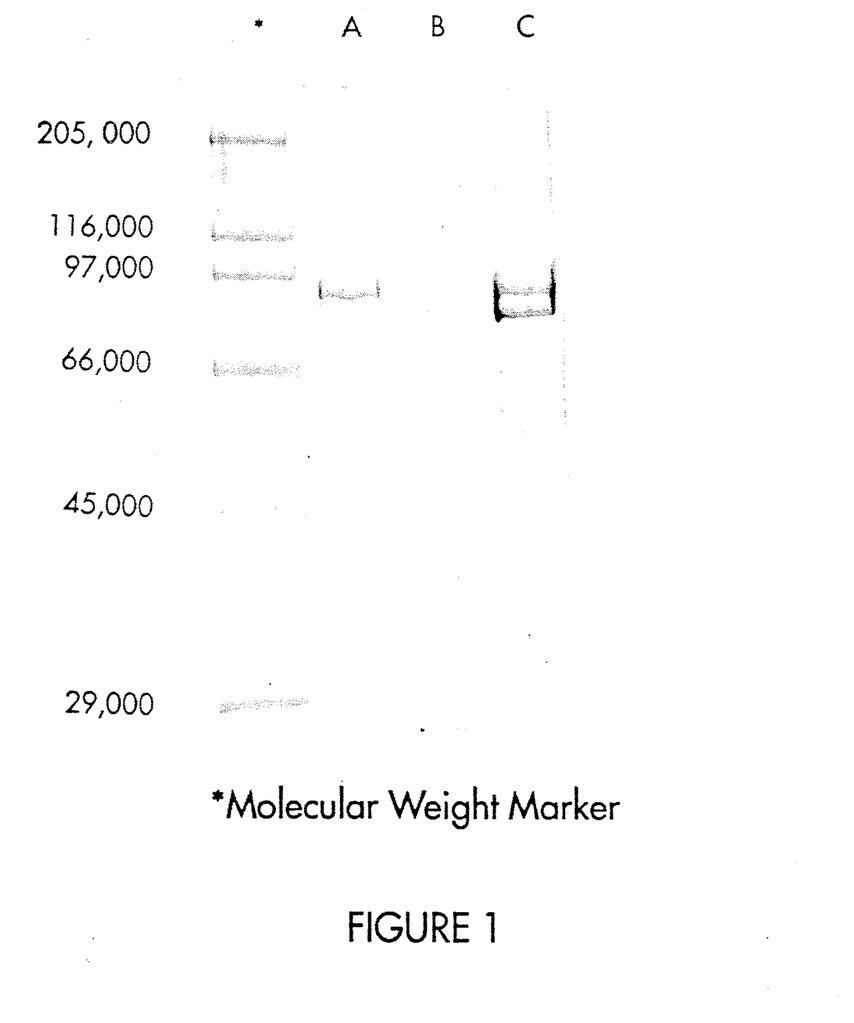
FIG. 1 is an autoradiograph of an SDS-PAGE analysis of DNA polymerase from *Thermus aquaticus*. The unmodified Taq DNA polymerase (85,000 dalton molecular weight) is illustrated in Lane A and the modified Taq DNA polymerase (80,000 dalton molecular weight) is illustrated in Lane B. Additionally, both polymerases were simultaneously purified as illustrated in Lane C. Apparent molecular weights are given on the left. Slight contamination of the 85,000 dalton Taq DNA polymerase with the 80,000 dalton polymerase is seen in Lane A.

Reference is now made to FIG. 1 for an SDS-PAGE analysis of the modified and unmodified Taq DNA polymerase from *Thermus aquaticus*. The relative amounts of the two polymerases vary considerably. Each purification procedure is optimized to manufacture one enzyme and minimize contamination by the other. As illustrated in FIG. 3, the 85,000 dalton molecular weight unmodified Taq DNA polymerase demonstrates significant exonuclease activity when used in DNA sequencing. If a mixture of the two polymerases is used for sequencing, the problems associated with an exonuclease activity are in direct proportion to the relative amount of the 85,000 molecular weight protein present. By modifying the previously described protocols, both enzymes can be purified simultaneously. Numerous enzyme preparations obtained during the development of this invention have shown that a mixture of the two polymerases can be manufactured. Preparations may contain very little of one or the other of the two enzymes depending on the incubation times during each early stage of purification.

Polyclonal antibodies raised against DNA polymerase I from *E. coli* recognize DNA polymerase from *Thermus aquaticus*. Polymerase samples were taken from various stages of the purification procedure and analyzed by SDS-PAGE and the Western Blotting technique known to the art. Both molecular weight polymerases are recognized by the antibodies, even in a protein sample where the polymerase only constitutes a small percentage of the total protein. Additional proteins with similar molecular weights have not consistently been identified with the antibodies, suggesting that there are not other stable, abundant polymerases.

Nature of the Modification

Without wishing to be constrained to one interpretation for the basis of the polymerase modification, it is believed that the polymerase modification involves cleavage by one or more proteases to inactivate a 5'-3' exonuclease. The inactivation of this domain allows the modified DNA polymerase to sequence DNA without the interference caused by the exonuclease. The modification clearly alters the apparent molecular weight of the polymerase, and the degree of molecular weight shift to the modified form varies inversely with the exonuclease activity as seen in DNA sequencing reactions. Thus, the amount of exonuclease activity is inversely proportional to the amount of 80,000 dalton molecular weight modified Taq DNA polymerase present. The more 80,000 dalton molecular weight protein that is present, the less exonuclease activity is seen. The nature of the modification may not be enzyme mediated proteolysis, but an alternative modification, such as protein oxidation, which would alter the apparent molecular weight.

More than one modification may be required for diminished exonuclease activity, but may not be correlated with shift in molecular weight. While part of the protein is lost, there could be modifications to the polymerase which do not cause a detectable shift in molecular weight.

Additional byproducts of the modification and treatment thereof may also be involved in the loss of exonuclease activity. For example, if a protein domain is cleaved from a polymerase and yet still contains functional exonuclease activity, the cleaved polypeptide would have to be purified away from the original protein. The purification would be included within the protocol described above. The end product is a functional DNA polymerase which sequences DNA with little demonstrated 5'-3' exonuclease activity.

The nature of the modification has heretofore been described as functionally reducing or eliminating a 5'-3' exonuclease activity. The activity may be "exonuclease-like" in its manifestations, but not actually be caused by a true exonuclease. Another biochemical or enzymatic activity which mimics an exonuclease activity in the sequencing application may be responsible. The modification clearly is associated with the enhanced ability of the modified polymerase to synthesize well defined products in the DNA reactions. For purposes of the present invention the word "exonuclease" as defined herein is intended to incorporate "exonuclease-like".

Uses for the Modified Taq DNA Polymerase

Enzymatic DNA Sequence Analysis

As described previously, one enzymatic method of DNA sequencing, known as the dideoxy or extension/termination method, is based on the ability of a DNA polymerase to extend a primer, hybridized to the template that is to be sequenced, until a strand-terminating nucleotide is incorporated. Each sequence determination is carried out as a set of four separate reactions which give four distinct populations of single-stranded DNA fragments. It is within the scope of the present invention to incorporate all four reactions in one reaction tube or alternatively in four separate reaction tubes. Each population of fragments begins at the same precise nucleotide position but has a variable terminus at one of four nucleotides: A (adenine), C (cytosine), G (guanine), or T (thymine). The synthesized fragments are separated by denaturing polyacrylamide gel electrophoresis and their lengths correspond to the presence of a particular nucleotide (A, C, G, or T) in the original template DNA. By knowing both the exact length (in nucleotides) of each fragment and which nucleotide terminates the fragment, the DNA sequence is delineated.

Two functional DNA polymerases can be purified from *Thermus aquaticus* strain YT1, with apparent molecular weights of about 80,000 and 85,000 daltons. When the 85,000 dalton protein is used for DNA sequencing, a significant 5'-3' exonuclease activity is detected. To produce reliable sequence data, it is critical that the 5' end of a synthesized strand be invariable for all four reactions. The exonuclease removes nucleotides from the 5' end of the synthesized DNA strand thereby making a variable terminus. It therefore becomes difficult to correlate the distinct size of a fragment with the presence of a particular nucleotide at the 3' end, i.e., to determine the DNA sequence. However, when the 80,000 dalton protein is used, there is little or no detectable 5'-3' exonuclease activity. Use of this modified Taq polymerase allows the distinct and unambiguous electrophoretic separation of DNA fragments and thereby generates reliable sequence data.

Taq DNA polymerase (both modified and unmodified) has been configured into a DNA sequencing system for enzymatic sequence analysis. This sequencing system, known as the TaqTrack ™ (Promega Corporation) sequencing system, is a modification of that described by Heiner, C., et al. (1988) *Applied Biosystems, Inc. DNA Sequencer Model 370 User Bulletin-Taq Polymerase: Increased Enzyme Versatility in DNA Sequencing*, and takes advantage of the intrinsic thermostable properties of the polymerase. The system uses either a radiolabeled oligonucleotide or an internally incorporated radiolabeled dNTP as the signal for autoradiographic detection. In the first case, before hybridizing a primer to the template, the sequencing primer is end-labeled using T4 polynucleotide kinase and an appropriate gamma-labeled nucleotide. A single radiolabel in the newly synthesized DNA strand is attached only to the first nucleotide. In the second case, a radiolabeled nucleotide is incorporated within the length of the newly synthesized DNA strand. Reference is made to Example 1 (infra.) and to *TaqTrack ™ Sequencing Systems Technical Manual*, Promega Corporation, printed Oct. 1988, which is incorporated herein by reference, for a detailed disclosure of this system.

In addition to the problems in DNA sequencing that are associated with an exonuclease type activity there are other commonly encountered difficulties. The modification that accounts for the shift in apparent molecular weight may also alter a number of subtle properties of the polymerase with the net result being that the enzyme produces better DNA sequence products. For example, a modification might additionally enhance the processivity or the rate of polymerization, change the binding affinity of the polymerase for the template or the nucleotide substrate, or slightly alter the thermostable properties of the enzyme. The modification may also improve the error rate of the polymerase. All of these types of modifications, no matter how slight, may cumulatively have a significant effect on DNA sequencing with the modified polymerase. While the exact number and type of modifications are not yet identified, there is an indisputable correlation between the modification of Taq DNA polymerase to the 80,000 dalton protein and the ability to synthesize more DNA fragments with well-defined 5' ends.

The modified Taq DNA polymerase sequencing system may be utilized for a wide variety of single-stranded (ss) and double-stranded (ds) templates such as amplified DNA, large ds DNA templates, such as lambda, GC-rich templates, and long poly (A) tails. The modified Taq DNA polymerase may also be used for thermocycling sequencing methods, DNA amplification, radioactively labeling DNA, nonradioactively labeling DNA, mutagenesis, second strand cDNA synthesis as well as many other applications where a polymerase is required with effectively no 5'-3' exonuclease activity.

Figure 2:
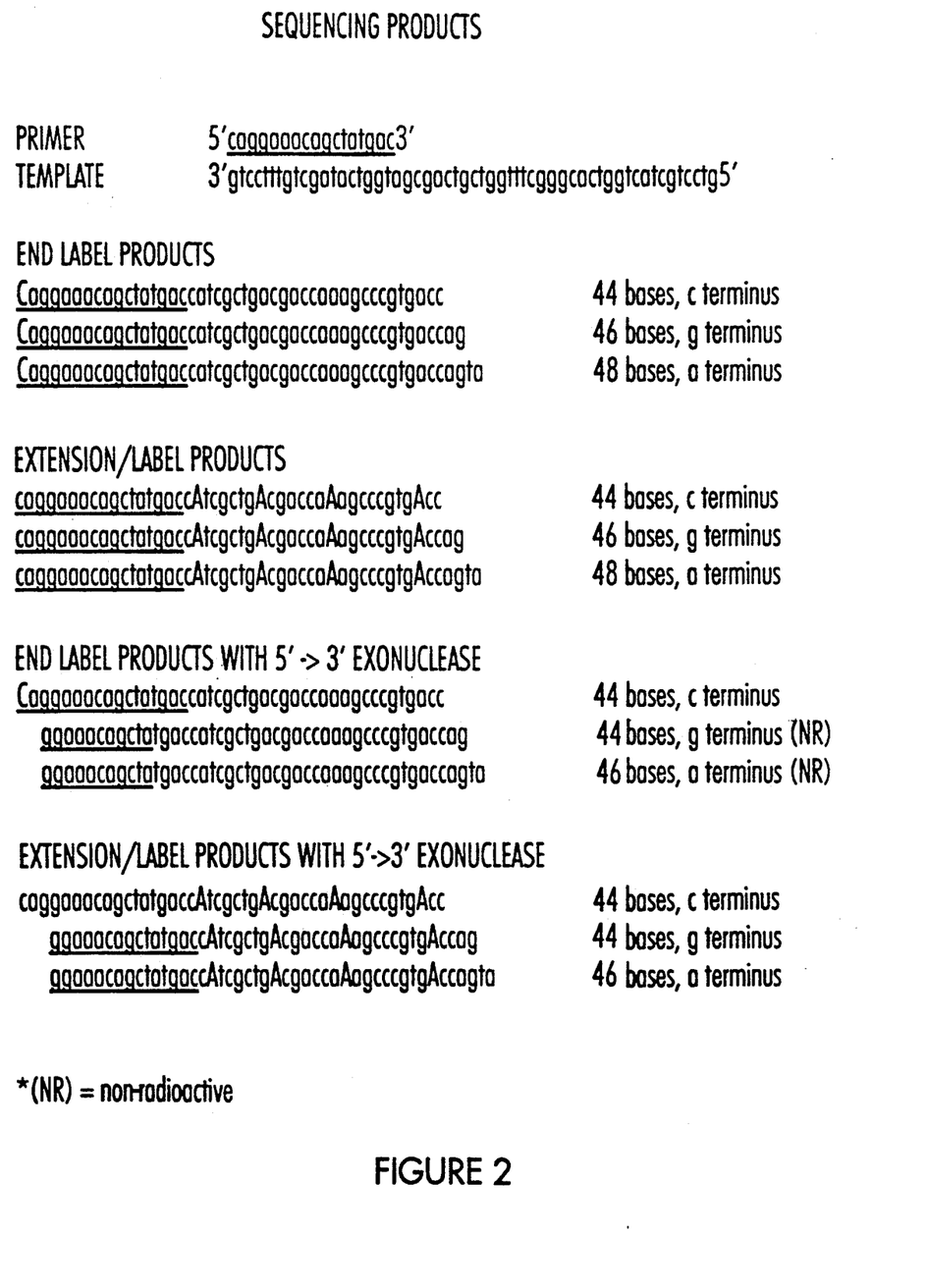
FIG. 2 illustrates the expected sequencing products with and without 5'-3' exonuclease. The primer and template DNA strands are shown at the top of the figure and four sets of synthesized strands are shown below. Each set contains three representative DNa strands which vary in length and terminate at C, G or A nucleotides. Primer sequences are underlined and radioactivity labeled nucleotides are in bold capital letters.

The presence of a 5'-3' exonuclease associated with Taq DNA polymerase is most clearly seen in sequencing denatured ds DNA although the effect is also seen when sequencing ss DNA. Reference is made to FIG. 2 which illustrates the expected products of both sequencing methods: end label and extension/label, and the expected products when a 5'-3' exonuclease is present. FIG. 2 illustrates how a contaminating 5'-3' exonuclease can produce two DNA strands which terminate at different nucleotides and yet have the same length, creating very ambiguous sequence data. In each case involving exonuclease, the first synthesized strand is unaltered and the other two strands are shortened by two nucleotides at the 5' end. The exonuclease-treated DNA strands may have the same length but terminate at different nucleotides. The end label strands which were treated with exonuclease are no longer radioactive and are therefore undetectable in autoradiographs.

Reference is now made to FIG. 3 which illustrates the actual DNA sequence data using the two different polymerases. Notice should be made to the difficulty in reading the sequence using the 85,000 dalton polymerase and the extension label protocol. The usefulness of the modified polymerase is clearly seen when using the extension label procedure.

An alternative DNA sequencing method which can incorporate the use of the modified Taq DNA polymerase of the present invention involves DN sequencing using alpha-thiodeoxynucleotides for sequence analysis. This protocol is generally described in Labeit, S. (1987), *Methods in Enzymology*, Vol. 155, p. 166-179) which is incorporated herein by reference. In this process, the modified Taq DNA polymerase is used to incorporate alpha-thiodeoxynucleotides into an elongating DNA strand which is then selectively degraded whereby at least a part of the nucleotide base sequence of the DNA molecule can be determined.

It is also within the scope of the present invention to incorporate the use of the modified Taq DNA polymerase into other DNA sequencing methods.

Thermocycling Reactions

The modified Taq DNA polymerase is stable during temperature thermocycling. Commonly, a thermocycling reaction is repeatedly cycled between up to 3 temperatures to denature, anneal and replicate the DNA while allowing the polymerase to remain catalytically active. A sequencing reaction using modified Taq DNA polymerase can be conveniently repeated by thermocycling. This increases the amount of radiolabeled products and strengthens the autoradiographic signal. Thermocycling is a method used for DNA amplification as described below.

DNA Amplification

A method for amplifying specific DNA sequences, called the polymerase chain reaction, works well with the thermostable modified Taq DNA polymerase. The amplification reaction, preferably a thermocycling reaction, uses two oligonucleotide primers which hybridize to opposite strands and flank the DNA region to be amplified. The annealed primers are aligned preferably with their 3' ends facing each other such that synthesis by modified Taq DNA polymerase extends across the region of the original DNA template between the two primers. Since each primer is complementary to one of the newly synthesized strands, each new strand can participate as a template in subsequent cycles of primer extension and segment amplification. Therefore, each thermocycle of strand denaturation, primer annealing and enzymatic extension doubles the amount of DNA from the previous cycle. Amplification is useful when a greater amount of nucleic acid is required for an analysis. Thus, this method has specific use for the detection of certain diseases. For example, a tiny sample of DNA from a body fluid containing a small quantity of the desired nucleic acid sequence may be amplified, processed according to techniques known to the art and analyzed via the Southern Blotting technique or DNA sequencing. Reference is made to Lo, Y-M.D., et al. (1988), *Nucleic Acids Research*, Vol. 16, No. 17, p. 8719 for a general discussion of the amplification procedure.

Radioactively Labeling DNA

The present invention also provides a method for labeling a DNA fragment which includes incubating the DNA fragment with modified Taq DNA polymerase and a labeled deoxyribonucleotide, and an appropriate buffer known to the art.

Mutagenesis

Mutagenesis is a method for introducing nucleotide substitutions or mutations within a DNA sequence to alter a gene or gene product. One method, commonly known as in vitro site-directed mutagenesis, involves introducing a mutation by the use of a synthetic oligonucleotide primer containing the desired mutation. The synthetic oligonucleotide is annealed to a template and acts as a primer for synthesis of a new DNA strand containing the mutation A polymerase such as modified Taq DNA polymerase is required for synthesis of the new strand. Subsequent amplification of the mutation can be accomplished using amplification or polymerase chain reaction (PCR) procedures. Reference is made to Higuchi, R., et al. (1988), *Nucleic Acids Research*, Vol. 16, No. 15, pp. 7351-7367. Reference is also made to Mole, Sara E., et al. (1989), *Nucleic Acids Research*, Vol. 17, No. 8, p. 319.

Another possible mutation method is random mutagenesis using modified Taq DNA polymerase. In this method, a sequence can be randomly mutated by misincorporation of nucleotides as the new DNA strand is synthesized.

Second Strand cDNA Synthesis

Modified Taq DNA polymerase may be used for the synthesis of double-stranded cDNA during cDNA cloning. The general method is described in Maniatis, T., et al. (1982) *Molecular Cloning—A Laboratory Manual*, Cold Spring Harbor Laboratory, using either DNA polymerase for *E. coli* or avian reverse transcriptase. Maintaining intact 5' ends on both DNA strands is critical in cDNA synthesis since only full length molecules provide all of the inherent sequence information from the original RNA molecule.

Nonisotopic Labeling of DNA

DNA is normally synthesized in vitro from four nucleotides, dATP, dCTP, dGTP, and dTTP. It is possible to modify these bases and use modified Taq DNA polymerase to recognize and incorporate them during DNA replication. This incorporation is the basis of non-isotopic labeling. The modified or 'labeled' bases may be incorporated using several methods involving DNA synthesis, including the polymerase chain reaction, fill-in reactions, or second strand synthesis from a primed template DNA. Reference is made to Maniatis, et al. (supra) and Mole, et al. (supra for a more detailed description of this method.

Kit for DNA Sequencing

The present invention is also directed to a kit for DNA sequencing, comprising the modified Taq DNA polymerase of the present invention and a reagent necessary for sequencing. The reagent may be deoxyribonucleotides, chain terminating agents, DNA sequencing primers, a reaction buffer and mixtures thereof.

The following examples are illustrative of the present invention and are not intended to limit the invention in any way.

EXAMPLES

Example 1

DNA Sequencing Method Utilizing End-Labeled Primer

This invention is directed to dideoxy sequence analysis using modified Taq DNA polymerase with an end-labeled oligonucleotide primer. Reference is made to *TaqTrack TM Sequencing Systems Technical Manual*, (*supra*), for a more detailed disclosure of this system.

There are three rapid and simple steps to this approach: 1) the sequencing primer is end-labeled in the presence of T4 polynucleotide kinase and an appropriate gamma-labeled nucleotide; 2) the labeled oligonucleotide and template are hybridized together; and 3) the extension/termination reaction is completed.

The use of an end-labeled primer offers several advantages in sequencing. The single radiolabel per molecule results in a uniform signal intensity throughout the autoradiograph. Internal labeling methods result in increasingly darker signals with increasing length of sequence, which often results in multiple X-ray film exposures and complicates the resolution of closely spaced DNA fragments. Degradation of the sequencing products by radiolysis is not a problem when using end-labeled sequencing primers. When radiolysis occurs, it simply removes the radioactivity from the 5' end of the newly synthesized strand, making it non-radioactive and therefore undetectable in the sequencing autoradiograph. Because of this the end-labeled primers and their extension products may be stored frozen at −20° C. for as long as a month and still generate clear sequence data.

Primer Radiolabeling Reaction

Different sequencing strategies require various oligonucleotide primer lengths depending on the temperature of hybridization and complexity of the template Generally, primers are 15-30 nucleotides long. The protocol is designed to label enough primer for 5 sets of double stranded or 10 sets of single stranded sequencing reactions. The experiment can be scaled proportionately according to the number of reactions to be performed. If the volume of the radiolabel or primer is in excess, it can be concentrated by drying in a vacuum desiccator and redissolving in the appropriate volume of buffer. The amount of radiolabel ($^{32}P$) in the reaction should be doubled if the isotope has decayed by one-half life (approximately 14 days).

In a microcentrifuge tube, 10 picomole (pmol) primer, 10 pmol gamma-labeled nucleotide, 1 ul T4 polynucleotide kinase buffer, 10X buffer (500 mM Tris-HCl at pH 7.5, 100 mM $MgCl_2$, 50 mM DTT, 1.0 mM spermidine), 0.5 ul T4 polynucleotide kinase (5–10 u/ul) and water to 10 ul is combined. After incubation at 37° C. for 10 minutes, the kinase is inactivated at 90° C. for 2 minutes and briefly centrifuged. If end-labeling with gamma-$^{35}S$, 20 units PNK is used while incubating for 4 hours. The end-labeled primers and their extension products may be stored frozen at 20° C. for as long as a month and still generate clear sequence data. The primer may be used directly without further purification.

Annealing Plasmid Template and Primer

The recommended amount of ds plasmid template to use per set of sequencing reactions is 1.6 pmol, which represents approximately 4 ug of 3–5 kb plasmid vector. Prior to annealing, the template should be alkali denatured and precipitated. The radiolabeled primer is annealed with the dsDNA plasmid template in an approximately 1:1 molar ratio. For each set of four sequencing reactions, 1.6 pmol of denatured plasmid template, 5.0 ul Taq DNA polymerase 5×buffer (250 mM Tris-HCl, pH 9.0 at 25° C., and 50 mM $MgCl_2$), 2.0 ul labeled primer (2 pmol), and water added to reach a final volume of 25 ul is mixed. The volume is incubated at 37° C. for 10 minutes prior to the extension/termination reactions.

Extension/Termination Reactions

For each set of sequencing reactions, four microcentrifuged tubes are labeled with a G, A, T and C. One ul of the corresponding d/ddNTP mix, as described below, is added to each tube and the tubes are capped to prevent evaporation. Six ul of the annealed primer/template mix is added to each of the four tubes containing the d/ddNTP mixes. After all of the tubes are ready, the Taq DNA polymerase is diluted to 2 u/ul with Taq DNA polymerase buffer which has been diluted to 1X with deionized water. Only enough enzyme required for immediate use should be diluted. For each set of four reactions, 4 ul of diluted enzyme are required. One ul of the diluted enzyme is added to the first tube of labeled primer/template/nucleotide mix. The mixture is mixed by pipetting up and down several times. The mixture is then immediately placed in a temperature of 70° C. for 10 minutes. The remaining tubes are prepared accordingly.

When the 10 minutes has expired, the first tube is removed in the series and 4 ul of a stop solution (10 mM NaOH, 95% formamide, 0.05% bromphenol blue, 0.05% xylene cyanole) is added and the tube is set at room temperature. The remaining tubes are prepared accordingly. Before loading a portion of each reaction onto a polyacrylamide sequencing gel, the reactions are heated at 90° C. for 5 minutes. Thus, each of the four (A, C, G and T) reaction tubes contains 1 ul d/ddNTP mixture, 6 ul annealed template/primer, 1 ul Taq DNA polymerase (diluted to 2 u/ul) and 4 ul stop solution. Single-stranded DNA or other denatured ds DNA may be substituted for the plasmid DNA in the above protocol. The recommended amount of ssDNA template to use per set of sequencing reactions is 0.8 pmol or approximately 2 ug of an 8 kb M13 template. The recommended amount of ds lambda phage template to use per set of sequencing reactions is 0.4 pmol, which represents 10 ug of an approximately 42 kb lambda vector. The radiolabeled primer is annealed with the dsDNA lambda template in an approximately 3:1 molar ratio while the annealing of the ssDNA is the same as described above for the denatured plasmid DNA.

EXAMPLE 2

DNA Sequencing By the Extension/Label Method

The previous example described DNA sequencing in which only one radioactive nucleotide was incorporated onto the 5' end of the newly synthesized strand. Example 2 describes a method in which several radioactive nucleotides are incorporated throughout the DNA strand and not at the first nucleotide position. This method involves a 2-step extension/labeling reaction where the hybridized primer is briefly extended in the presence of radioactive nucleotides with low concentrations of non-radioactive dNTPs. This mainly incorporates the radioactivity into a short region of the newly synthesized DNA strand adjacent to the primer. After the extension/label reaction, the same method of extension termination as described above is completed. This protocol is especially suited for use of $^{35}$S in DNA sequencing because the number of radioactive nucleotides per DNA strand is increased over the end-labeled method. The two-step extension/labeling protocol described here uses a separate extension/labeling reaction to incorporate the [alpha-$^{35}$S] dATP label. This protocol gives high label incorporation making overnight exposures possible when sequencing with $^{35}$S.

Annealing the Template and Primer

The primer is annealed with the template in an approximately 1:1 molar ratio. For each set of four sequencing reactions, the following reagents are mixed in a microcentrifuge tube and incubated at 37° C. for approximately 10 minutes: 1.9 pmol dsDNA alkali denatured (approximately 4 ug of 3.2 kb template), 2.0 pmol primer (approximately 16 ng of a 24mer), 5.0 ul modified Taq DNA polymerase in 5×buffer, 2.0 ul extension mix (7.5 uM dGTP, dTTP, dCTP) and water to 25 ul. While this reaction is incubating, the nucleotide tubes are prepared by labeling 4 microcentrifuge tubes: G, A, T, and C and adding 1 ul of an appropriate d/ddNTP mix to each tube. The tubes are stored on ice or at 4° C.

Extension/Labeling Reaction

Two ul of [alpha-35S]dATP (1000 Ci/mmol) or [alpha-$^{32}$P] dATP (800 Ci/mmol) are added to the annealed primer/template mixture. 1.5 ul of modified Taq DNA polymerase (4-5 u/ul) is added and incubated at 37° C. for approximately 5 minutes. In order to read DNA sequence closer to the primer, the time of the extension/labeling reaction should be shortened.

Termination Reaction

When the extension reaction is complete, 6 ul of the mixture is aliquoted to each tube (G, A, T, C) containing the d/ddNTP mixture and mixed briefly by pipetting up and down The mixture is incubated at 70°-74° C. for approximately 5 minutes. Four ul of stop solution is added to each tube and the reactions are heated to 90° C. for 5 minutes immediately before loading on a sequencing gel. Three ul of each reaction is then loaded onto a denaturing polyacrylamide gel.

Interpretation of Sequenced Data

In the end-labeled method (Example 1), a 5'-3' exonuclease removes the radioactive nucleotide from the 5' end of the newly synthesized strand. This makes the truncated strand non-radioactive and therefore undetectable by autoradiography. In this method, few artifacts should be seen due to the 5'-3' exonuclease but the autoradiographic signal intensity may be diminished due to fewer strands being labeled. In the extension label reaction (Example 2), all newly synthesized strands remain radioactively labeled even after nucleotides are removed from the 5' end. The exonuclease shortens the DNA strands from the 5' end thereby allowing 2 strands which terminate at different nucleotide positions to resolve as identically sized fragments. Likewise, two strands may terminate at the same nucleotide and have different lengths. This leads to ambiguities in delineating the DNA sequence.

The clear advantage of using modified Taq DNA polymerase is DNA sequencing as illustrated in FIG. 3. The sequence data is presented using modified Taq DNA polymerase, unmodified Taq DNA polymerase and a mixture of the two enzymes in both sequencing methods: end label and extension/label. When using the end label method, all three produce sequence data. When using the extension/label method, the modified enzyme provides distinct sequence data with very few artifacts. Both enzymes produce sequence data with several ambiguities and the unmodified polymerase produces nearly unintelligible sequence data.

Example 3

Thermocycling Sequencing Method

A sequencing reaction using modified Taq DNA polymerase may be repeatedly thermocycled through temperatures which 1) denature the template DNA, 2) anneal the primer to the template, and 3) allow strand elongation and dideoxy termination. After one sequencing reaction is complete, the newly synthesized products are thermally denatured from the template strand. The template is then free to function in another set of sequencing reactions, beginning with the primer hybridization. Using the end-labeled primer method described above, a supercoiled plasmid may be sequenced without prior alkali denaturation.

The end-labeled reaction mixture is prepared and heated at 70°-74° C. at 2 minutes, at 95° C. for 1 minute, and at 45° C. for 1 minute. This cycle of temperatures is repeated 1-90 times and each cycle yields a set of sequencing products. There is a significant accumulation of newly synthesized DNA strands. This increases the amount of incorporated radioactivity and thereby reduces the autoradiographic exposure time. The temperature cycling further facilitates sequencing difficult DNA templates containing stable secondary structures.

Example 4

DNA Amplification Using Modified Taq DNA Polymerase

An amplification reaction involves mixing approximately 0.001-1 ng template DNA, 10 ul 10×amplification buffer (500 mM KCl, 100 mM Tris-HCl at pH 9.0 and temperature 25° C., 15 mM $MgCl_2$, 0.1% porcine gelatin, and 1% Triton X-100), 1 ug each of two appropriate amplification primers, 200 uM each dATP, dCTP, dGTP and dTTP, 2.5 units of modified Taq DNA polymerase and water to 100 ul. The reaction is generally cycled 1-90 times for 1 minute at 95° C., 1 minute at 45° C., and 1 minute at 70° C. The incubation time at 70° C. may vary depending on the size of the amplified segment. The hybridization temperature will vary depending on the length of the oligonucleotide primers. Reference is made to Lo, Y-M.D. (supra).

Modified Taq DNA polymerase is thermostable to allow for its use in the polymerase chain reaction. The 5' ends of the amplified DNA segments would not be degraded during the amplification reaction using modified Taq DNA polymerase as they would be using the unmodified polymerase. The result would be that the amplified segments would have more clearly defined termini and more full length products.

Example 5

Radioactively Labeling DNA Using Modified Taq DNA Polymerase

To radioactively label DNA, an amplification reaction is performed using protocol described above with radioactive nucleotide supplemented in the nucleotide mixture. Depending on the specific activity required in the radioactive labeling, different amounts of radionucleotides may be incorporated.

DNA may also be radioactively labeled using the method described above for determining the unit activity of Taq DNA polymerase. Any appropriately primed DNA can be substituted for the calf thymus DNA, and radioactive nucleotide concentrations can be adjusted to produce the correct specific activity product. The modified Taq DNA polymerase offers the advantage in radiolabeling DNA and leaving the 5' ends of DNA molecules intact.

It is understood that the invention is not confined to the particular construction and arrangement herein illustrated and described, but embraces such modified forms thereof as come within the scope of the following claims.

What is claimed is:

1. A method for determining the nucleotide base sequence of a DNA molecule, comprising:
   a) hybridizing a primer to a DNA template molecule to be sequenced;
   b) extending the primer with a Taq DNA polymerase having an apparent molecular weight of about 80,000 daltons and substantially no 5'-3' exonuclease activity;
   c) incorporating a strand terminating nucleotide onto the extended primer under conditions to yield a distinct population of nucleotide fragments beginning on the same nucleotide position for all populations and having a variable terminus at one of the following four nucleotide bases: A, C, G and T; and
   d) separating the synthesized fragments according to their size, whereby at least a part of the nucleotide base sequence of the DNA molecule can be determined.

2. The method of claim 1 wherein the primer is an oligonucleotide primer.

3. The method of claim 1 wherein the determination of the DNA sequence further comprises a set of four different sequencing reactions, wherein each sequencing reaction contains a different strand terminating nucleotide which terminates nucleotide synthesis at a specific nucleotide base wherein each reaction yields a distinct population of nucleotide fragments.

4. The method of claim 3 wherein each sequencing reaction contains the following four deoxyribonucleotide triphosphates: dATP, dCTP, dGTP, dTTP; and each sequencing reaction contains a limiting amount of strand terminating nucleotide.

5. The method of claim 4 wherein the strand terminating nucleotide is selected from the following dideoxyribonucleotide triphosphates: ddATP, ddCTP, ddGTP, and ddTTP.

6. The method of claim 5 further comprising adjusting the concentration of the dideoxyribonucleotide triphosphate depending on the number of nucleotide bases to be sequenced.

7. The method of claim 1 further comprising incorporating a radioactive nucleotide in the elongating DNA strand to detect the sequencing products.

8. The method of claim 7 comprising:
   a) hybridizing the primer to a DNA template to be sequenced;
   b) extending the primer with the Taq DNA polymerase in four separate reactions, each reaction containing one alpha-$^{32}$P-labeled deoxynucleotide triphosphate selected from the group consisting of dATP, dCTP, dGTP, and dTTP; each reaction further containing unlabeled dATP, dCTP, dGTP, and dTTP; each reaction further comprising a different one of a chain terminating dideoxyribonucleotide triphosphate selected from the group consisting of ddATP, ddCTP, ddGTP, and ddTTP;
   c) resolving the products of the reactions on a gel using high-resolution denaturing polyacrylamide gel electrophoresis; and
   d) employing radioactivity of the $^{32}$P incorporated into the reaction products to produce a detectable image of the gel to determine the DNA sequence.

9. The method of claim 1 further comprising incorporating a nonradioactively-labeled nucleotide in the elongating DNA strand to detect the sequencing products.

10. The method of claim 9 wherein the nonradioactively-labeled nucleotide is selected from the group consisting of biotin and fluorescently labeled nucleotides.

11. A method for determining the nucleotide base sequence of a DNA molecule, comprising:
   a) hybridizing a primer to a DNA template molecule to be sequenced;
   b) extending the primer with a Taq DNA polymerase having an apparent molecular weight of about 80,000 daltons and substantially no 5'-3' exonuclease activity;
   c) incorporating alpha-thiodeoxynucleotides onto the extending primer with the modified Taq DNA polymerase, wherein the extended primer is selectively degraded to yield a distinct population of nucleotide fragments beginning at the same nucleotide position for all populations and having a variable terminus at one of the following four nucleotide bases: A, C, G and T; and d) separating the synthesized fragments according to size, whereby at least a part of the nucleotide base sequence of the DNA molecule can be determined.

12. A method for determining the nucleotide base sequence of a DNA molecule, comprising:
   a) hybridizing a primer to a DNA template molecule to be sequenced;
   b) extending the primer with a Taq DNA polymerase having an apparent molecular weight of about 80,000 daltons and substantially no 5'-3' exonuclease activity;
   c) incorporating a strand terminating nucleotide onto the extended primer, wherein the determination of the DNA sequence is accomplished by a set of four different sequencing reactions, wherein each sequencing reaction contains a different strand terminating nucleotide which terminates nucleotide synthesis at a specific nucleotide base wherein each reaction yields a distinct population of nucleotide fragments beginning on the same nucleotide position for all populations, but having a variable terminus at one of the following four nucleotide bases: A, C, G and T; and
   d) separating the synthesized fragments according to their size, whereby at least a part of the nucleotide base sequence of the DNA molecule can be determined.

13. The method of claim 12, wherein the Taq DNA polymerase produces readable DNA sequence data for up to 1000 nucleotide bases before dissociating.

14. The method of claim 12 wherein the Taq DNA polymerase produces readable DNA sequence data for up to 500 nucleotide bases before dissociating.

15. The method of claim 12 wherein the synthesized fragments are separated by denaturing polyacrylamide gel electrophoresis.

16. The method of claim 12 wherein each sequencing reaction contains the following four deoxyribonucleotide triphosphates: dATP, dCTP, dGTP, dTTP; and each sequencing reaction contains a limiting amount of a strand terminating nucleotide selected from one of the following dideoxyribonucleotide triphosphates: ddATP, ddCTP, ddGTP, ddTTP.

17. The method of claim 16 further comprising adjusting the concentration of the dideoxyribonucleotide triphosphates depending on the number of nucleotide bases to be sequenced, wherein the concentrations are optimized for incorporation by the modified Taq DNA polymerase.

18. The method of claim 12 further comprising incorporating a radioactive nucleotide in the elongating DNA strand to detect the sequencing products.

19. The method of claim 12 further comprising incorporating a nonradioactively-labeled nucleotide in the elongating DNA strand to detect the sequencing products.

20. The method of claim 19 wherein the nonradioactively-labeled nucleotide is selected from the group consisting of biotin and fluorescently labeled nucleotides.

21. The method of claim 18 further comprising end-labeling the primer in the presence of an effective end-labeling amount of a radiolabeled nucleotide prior to hybridizing the DNA template.

22. The method of claim 21 the radiolabeled nucleotide is labeled with gamma$^{35}$S or gamma $^{32}$P.

23. The method of claim 21 further comprising end-labeling the primer in the presence of an effective end-labeling amount of a nonradiolabeled nucleotide prior to hybridizing the DNA template.

24. The method of claim 12 wherein the DNA template molecule is selected from the group consisting of single-stranded DNA molecules and denatured double-stranded DNA molecules.

25. The method of claim 18 further comprising extension-labeling the primer in the presence of an effective radioactive nucleotide and non-radioactive deoxyribonucleotide triphosphates.

26. In an enzymatic CNA synthesis reaction wherein a primer is hybridized to a template DNA template in a reaction catalyzed by a DNA polymerase, the improvement comprising catalyzing the extension of primer with a Taq DNA polymerase having an apparent molecular weight of about 80,000 daltons and substantially no 5'-3' exonuclease activity.

27. A method of amplifying a DNA sequence comprising:
   (a) annealing a first and second primer to opposite strands of a double stranded DNA template molecule, and
   (b) thermocycling the annealed mixture with a Taq DNA polymerase having an apparent molecular weight of about 80,000 daltons and substantially no 5'-3' exonuclease activity.

28. The method of claim 27 wherein the first and second primers are aligned with their 3' ends facing each other.

29. A thermocycling DNA sequencing method comprising one or more repetitions of the following steps:
   a) denaturing the DNA sequence under suitable denaturing conditions to form single-stranded DNA sequence segments;
   b) annealing the DNA sequence under conditions sufficient to hybridize a primer to a template of a DNA sequence segment; and
   c) replicating the DNA sequence segment by extending the primer with a Taq DNA polymerase having an apparent molecular weight of about 80,000 daltons and substantially no 5'-3' exonuclease activity.

30. A method for determining the order in which nucleotide bases are arranged within a length of a nucleic acid strand, comprising:
   a) incubating the nucleic acid strand with a nucleotide triphosphate selected from the group consisting of dATP, dCTP, dGTP, dTTP, and a primer for each sequence;
   b) incubating the nucleic acid strand at the same time with a Taq DNA polymerase having an apparent molecular weight of about 80,000 daltons and substantially no 5'-3' exonuclease activity for an effective time and at an effective temperature to catalyze the nucleotide triphosphate to form primer extension products complementary to each nucleic acid strand.

31. The method of claim 30 wherein the primer is radiolabeled for detection.

32. The method of claim 30 wherein the incorporated nucleotide triphosphate has a radiolabel.

33. The method of claim 32 wherein before hybridizing primer to the template, the sequencing primer is end-labeled.

34. The method of claim 33 wherein the sequencing primer is end-labeled in the presence of T4 polynucleotide kinase and an appropriate gamma-labeled nucleotide.

35. The method of claim 32 wherein the radiolabeled nucleotide is incorporated throughout the length of the newly synthesized nucleic acid strand.

36. The method of claim 30 further comprising incorporating a nonradioactively-labeled nucleotide in the elongating DNA strand to detect the sequencing products.

37. The method of claim 36 wherein the nonradioactively-labeled nucleotide is selected from the group consisting of biotin and fluorescently labeled nucleotides.

38. The method of claim 30 wherein the reaction proceeds at a temperature up to about 96° C.

39. The method of claim 30 wherein the reaction proceeds at a temperature between 70° and 80° C.

40. The method according to claim 30 wherein the nucleic acid strand is denatured double-stranded DNA or single-stranded DNA.

41. A method for labeling DNA molecules comprising:
    a) annealing a primer to a DNA template molecule; and
    b) incubating a nucleotide in the annealed mixture of step a) with a Taq DNA polymerase having an apparent molecular weight of about 80,000 daltons and substantially no 5'-3' exonuclease activity under effective conditions to incorporate the labeled nucleotide into the DNA molecule.

42. The method of claim 40 wherein the labeling nucleotide is selected from the group consisting of radioactive nucleotides and nonradioactive nucleotides.

43. A method for site-directed in vitro mutagenesis within a DNA sequence comprising annealing a primer containing a desired mutation sequence to a DNA template molecule and extending the primer with a Taq DNA polymerase having a molecular weight of about 80,000 daltons and substantially no 5'-3' exonuclease activity, such that the primer synthesizes a new DNA sequence containing the mutation.

44. A method for random in vitro mutagenesis within a DNA sequence comprising annealing a primer to the DNA sequence in the presence of a Taq DNA polymerase having a molecular weight of about 80,000 daltons and substantially no 5'-3' exonuclease activity, under conditions in which the DNA sequence is randomly mutated as the new DNA strand is synthesized.

45. A kit for DNA sequencing, comprising:
    a) Taq DNA polymerase having an apparent molecular weight of about 80,000 daltons and substantially no 5'-3' exonuclease activity; and
    b) a reagent necessary for sequencing.

46. The kit of claim 45 wherein the reagent is selected from the group consisting of deoxyribonucleotides, chain terminating agents, DNA sequencing primers, a reaction buffer and mixtures thereof.

* * * * *

UNITED STATES PATENT AND TRADEMARK OFFICE
CERTIFICATE OF CORRECTION

PATENT NO. : 5,108,892

DATED : April 28, 1992

Page 1 of 2

INVENTOR(S) : Thomas J. Burke, David V. Thompson, Sandra L. Spurgeon

It is certified that error appears in the above-identified patent and that said Letters Patent is hereby corrected as shown below:

On the title page, Under Publications "Bethesda Research Laboratories" reference, line 3, "Test" should be --Taq--.

Under Publications: in the "Heiner, C. et al." reference, line 2, "Taqu" should be --Taq--.

Under Publications: in the "Lawyer, F.C. et al." line 1, "1988" should be --1989--.

Column 8, Lines 38-44, should be a single paragraph.

Column 15, Line 37, "DN" should be --DNA--.

Column 17, Line 64, "template" should be --template.--.

Column 19, Line 56, "[alpha-35S]" should be --[alpha-$^{35}$S]--.

Column 19, Line 68, "down" should be --down. --.

UNITED STATES PATENT AND TRADEMARK OFFICE
CERTIFICATE OF CORRECTION

PATENT NO. : 5,108,892
DATED : April 28, 1992
INVENTOR(S) : Thomas J. Burke, David V. Thompson, Sandra L. Spurgeon It is certified that error appears in the above-identified patent and that said Letters Patent is hereby corrected as shown below:

Column 23, Line 50, delete "modified."

Column 24, Line 13, "CNA" should be --DNA--.

Column 24, Line 14, after "DNA" insert --molecule and the primer is extended on said--.

Signed and Sealed this

Twentieth Day of July, 1993

Attest:

MICHAEL K. KIRK

*Attesting Officer*  *Acting Commissioner of Patents and Trademarks*